(12) United States Patent
Cano et al.

(10) Patent No.: US 10,489,555 B2
(45) Date of Patent: *Nov. 26, 2019

(54) MEDICATION PROCESSING KIOSK

(71) Applicant: QUALANEX, LLC, Gurnee, IL (US)

(72) Inventors: Derek Cano, Broomfield, CO (US);
Donald W. Stark, Arvada, CO (US);
Alan Lewis Dubois, Louisville, CO (US); Dan Ezell, Buffalo Grove, IL (US)

(73) Assignee: QUALANEX, LLC, Gurnee, IL (US)

( * ) Notice: Subject to any disclaimer, the term of this patent is extended or adjusted under 35 U.S.C. 154(b) by 187 days.

This patent is subject to a terminal disclaimer.

(21) Appl. No.: 15/402,597

(22) Filed: Jan. 10, 2017

(65) Prior Publication Data
US 2017/0199983 A1    Jul. 13, 2017

Related U.S. Application Data

(63) Continuation-in-part of application No. 14/805,370, filed on Jul. 21, 2015, now Pat. No. 9,539,179.

(Continued)

(51) Int. Cl.
*G06F 19/00* (2018.01)
*G07F 9/02* (2006.01)
(Continued)

(52) U.S. Cl.
CPC ............ *G06F 19/3462* (2013.01); *A61J 7/02* (2013.01); *G07F 9/023* (2013.01);
(Continued)

(58) Field of Classification Search
CPC .... G06F 19/3456; G06F 19/3462; A61J 7/02; G07F 17/0092
See application file for complete search history.

(56) References Cited

U.S. PATENT DOCUMENTS 5,468,110 A * 11/1995 McDonald ........... B65G 1/1371
                                                 414/268
5,884,806 A *  3/1999 Boyer ...................... A61J 7/02
                                                 221/13

(Continued)

OTHER PUBLICATIONS

Non-Final Office Action on U.S. Appl. No. 14/805,370, dated May 11, 2016 May 11, 2016.

(Continued)

*Primary Examiner* — Timothy R Waggoner
(74) *Attorney, Agent, or Firm* — Foley & Lardner LLP

(57) ABSTRACT

A kiosk includes a processor configured to receive, from a user interface device, medication information and determine, via a database, that medication associated with the medication information satisfies criteria. The processor is also configured to receive, from a first camera, an image of the medication and to determine that the image of the medication satisfies a visual criterion. The processor is further configured to receive, from the scale, a weight of the medication and to determine that the weight of the medication satisfies an expected weight criterion. The processor is also configured to cause a display to display an indication that the medication satisfies the criteria based at least in part on the determination that the image of the medication satisfies the visual criterion and the determination that the weight of the medication satisfies the expected weight criterion.

18 Claims, 10 Drawing Sheets

Related U.S. Application Data

(60) Provisional application No. 62/027,179, filed on Jul. 21, 2014.

(51) Int. Cl.
*A61J 7/02* (2006.01)
*G07F 17/00* (2006.01)
*G16H 40/63* (2018.01)
*G16H 20/13* (2018.01)

(52) U.S. Cl.
CPC ......... *G07F 17/0092* (2013.01); *G16H 20/13* (2018.01); *G16H 40/63* (2018.01)

(56) References Cited

U.S. PATENT DOCUMENTS

| | | | |
|---|---|---|---|
| 6,711,460 B1 | 3/2004 | Reese | |
| 6,769,228 B1 * | 8/2004 | Mahar | B65B 61/20 53/155 |
| 7,599,516 B2 | 10/2009 | Limer | |
| 7,930,064 B2 * | 4/2011 | Popovich, Jr. | G07F 17/0092 221/2 |
| 8,271,128 B1 * | 9/2012 | Schultz | A61J 7/02 700/236 |
| 8,374,887 B1 | 2/2013 | Alexander | |
| 8,827,112 B2 | 9/2014 | Yuyama | |
| 8,833,602 B1 | 9/2014 | Balasubramanian | |
| 9,033,006 B2 | 5/2015 | Perazzo | |
| 9,539,179 B2 * | 1/2017 | Cano | A61J 7/02 |
| 2001/0041968 A1 * | 11/2001 | Hamilton | A61J 7/02 702/128 |
| 2004/0088187 A1 | 5/2004 | Chudy et al. | |
| 2014/0355849 A1 * | 12/2014 | Brossette | G06F 19/3462 382/128 |
| 2015/0302255 A1 * | 10/2015 | Gershtein | G06K 9/00 382/128 |

OTHER PUBLICATIONS

Notice of Allowance on U.S. Appl. No. 14/805,370 dated Sep. 6, 2016.

* cited by examiner

MEDICATION PROCESSING KIOSK

CROSS REFERENCE TO RELATED APPLICATIONS

This application is a continuation-in-part of U.S. patent application Ser. No. 14/805,370, filed Jul. 21, 2015, which claims priority to U.S. Provisional Patent Application No. 62/027,179, filed on Jul. 21, 2014, both of which are incorporated herein by reference in their entirety.

TECHNICAL FIELD

Embodiments described herein relate generally to an interactive kiosk for receiving medication, and more specifically to an interactive kiosk for receiving, counting, imaging, and labeling medication liquids and capsules.

BACKGROUND

The following description is provided to assist the understanding of the reader. None of the information provided or references cited is admitted to be prior art. When a pharmacy or other organization has unsold or surplus medications, it may return those medications to the manufacturer thereof for credit or reimbursement. Pharmaceutical manufacturers may also recall medications from pharmacies because such medications are defective, mislabeled, or otherwise not suitable for use. A pharmacy or other organization may also accept recalled, unused, or partially used pharmaceutical prescriptions from its customers. In such instances, it is often a time-consuming process to verify the medication, count the number of pills, capsules, injectable medicine, or volume of liquid being returned, and address and ship the medication to the origin company or its designated agent or contractor.

SUMMARY

An illustrative kiosk includes a user interface device configured to receive information from a user, a display configured to display information to the user, a first camera, a scale, a transceiver configured to communicate with a database, and a processor operatively coupled to the user interface device, the display, the first camera, the scale, and the transceiver. The processor is configured to receive, from the user interface device, medication information and determine, via the database, that medication associated with the medication information satisfies criteria. The criteria are provided to the database by a manufacturer of the medication. The criteria include an expected weight criterion of the medication and a visual criterion of the medication or its packaging. The processor is also configured to receive, from the first camera, an image of the medication or its packaging and to determine, or enable a user of the kiosk to determine, that the image of the medication or its packaging satisfies the visual criterion. The processor is further configured to receive, from the scale, a weight of the medication and to determine that the weight of the medication satisfies the expected weight criterion. The processor is also configured to cause the display to display an indication that the medication satisfies the criteria based at least in part on the determination that the image of the medication satisfies the visual criterion and the determination that the weight of the medication satisfies the expected weight criterion. The processor is also configured to cause the transceiver to transmit the medication information, one or more images of the medication, and the weight of the medication to the database.

An illustrative method includes receiving, from a user interface device that is configured to receive information from a user, medication information and determining, via a remote database, that medication associated with the medication information satisfies criteria. The criteria are provided to the remote database by a manufacturer of the medication. The criteria include an expected weight criterion of the medication and a visual criterion of the medication or its packaging. The method also includes receiving, from a first camera, an image of the medication or its packaging and determining, or enabling the user to determine, that the image of the medication or its packaging satisfies the visual criterion. The method further includes receiving, from a scale, a weight of the medication and determining that the weight of the medication satisfies the expected weight criterion. The method also includes causing a display to display an indication that the medication satisfies the criteria based at least in part on the determination that the image of the medication satisfies the visual criterion and the determination that the weight of the medication satisfies the expected weight criterion. The method further includes transmitting, to the remote database, the medication information, one or more images of the medication, and the weight of the medication.

A kiosk according to an embodiment of the present disclosure includes a housing; a touch screen on the housing, the touch screen configured to receive input information from a user of the kiosk; a label printer on the housing, the label printer configured to print output information from the kiosk; a pill drop opening; a pill chute; a drive tube having an entry opening and an exit opening, wherein the drive tube is tubular, has an axis extending through a longitudinal axial centerline of the drive tube, and has an inside surface comprising a helical flute, wherein the entry opening is in communication with the pill chute, and wherein the exit opening is higher than the entry opening such that the axial centerline of the drive tube is inclined; a motor configured to rotate the drive tube to separate and convey pills received through the pill drop opening and the pill chute; and an optical counter configured to count the pills as the pills fall from the exit opening of the drive tube.

A kiosk according to an embodiment of the present disclosure may include a processor within the housing, the processor communicably coupled to the touch screen, the label printer, the motor, and the optical counter, wherein the processor is configured to: receive information about the pills from the touch screen based upon user input; selectively actuate the motor to convey the pills from the entry opening to the exit opening; receive and store count information about a number of the pills from the optical counter; and instruct the label printer to print a label displaying the count information.

A kiosk according to an embodiment of the present disclosure may further include a camera; and a scale, wherein the processor further communicably coupled to the camera and the scale, and wherein the processor is further configured to: receive information about a liquid medicine; receive and store information about a weight of the liquid medicine from the scale while the liquid medicine is placed upon the scale; receive and store visual information from the camera about the liquid medicine while the liquid medicine is placed upon the scale.

According to some embodiments of the present disclosure, the axial centerline of the drive tube is inclined along a direction from a rear of the kiosk toward a front of the kiosk. In some cases, the touch screen is located at the front of the kiosk. The kiosk may include a catch bin located at the front of the kiosk, wherein the catch bin is configured to receive the pills after the pills have fallen from the exit opening of the drive tube, according to embodiments of the present disclosure. While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
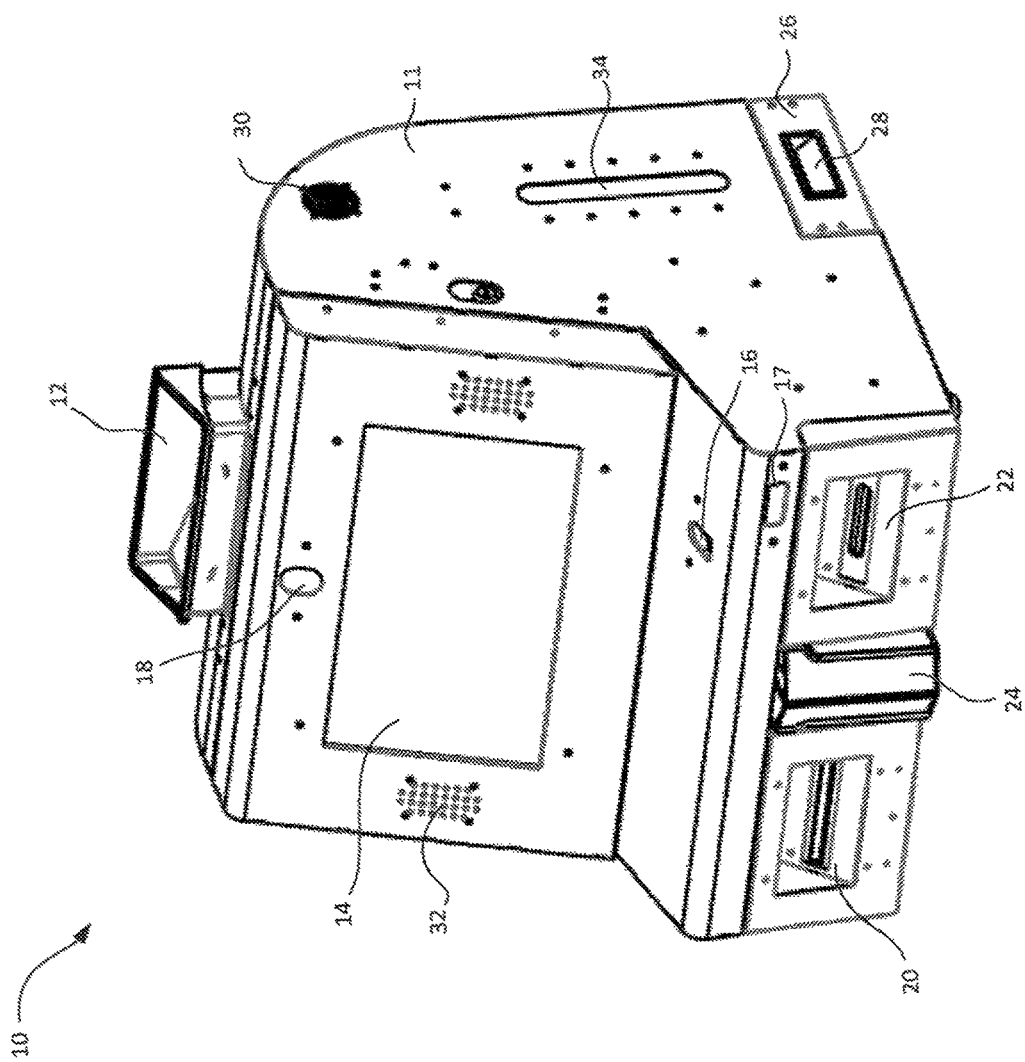
FIG. 1 illustrates a front perspective view of an interactive kiosk according to an illustrative embodiment.
Figure 2:
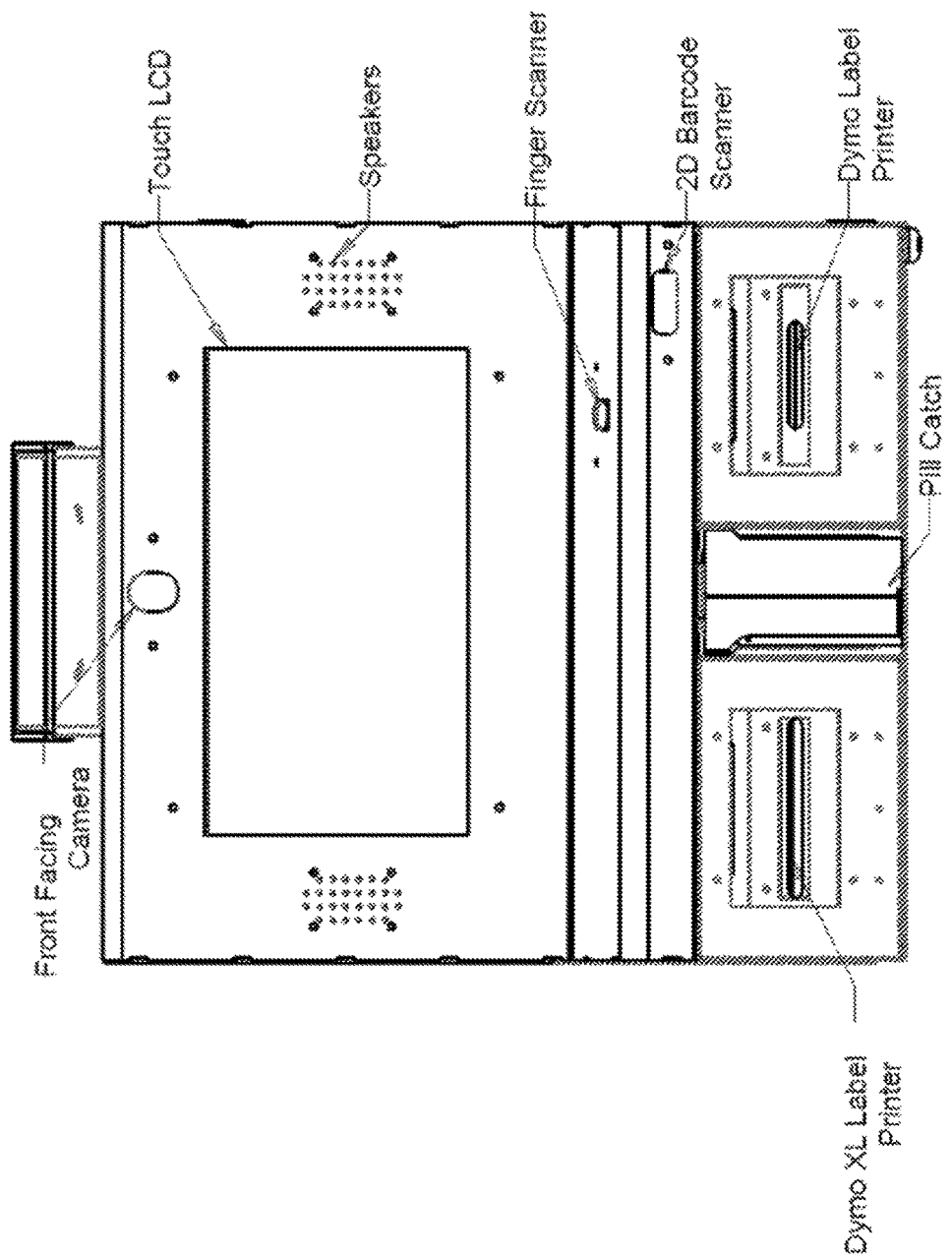
FIG. 2 illustrates a front elevation view of the interactive kiosk of FIG. 1, according to an illustrative embodiment.
Figure 3:
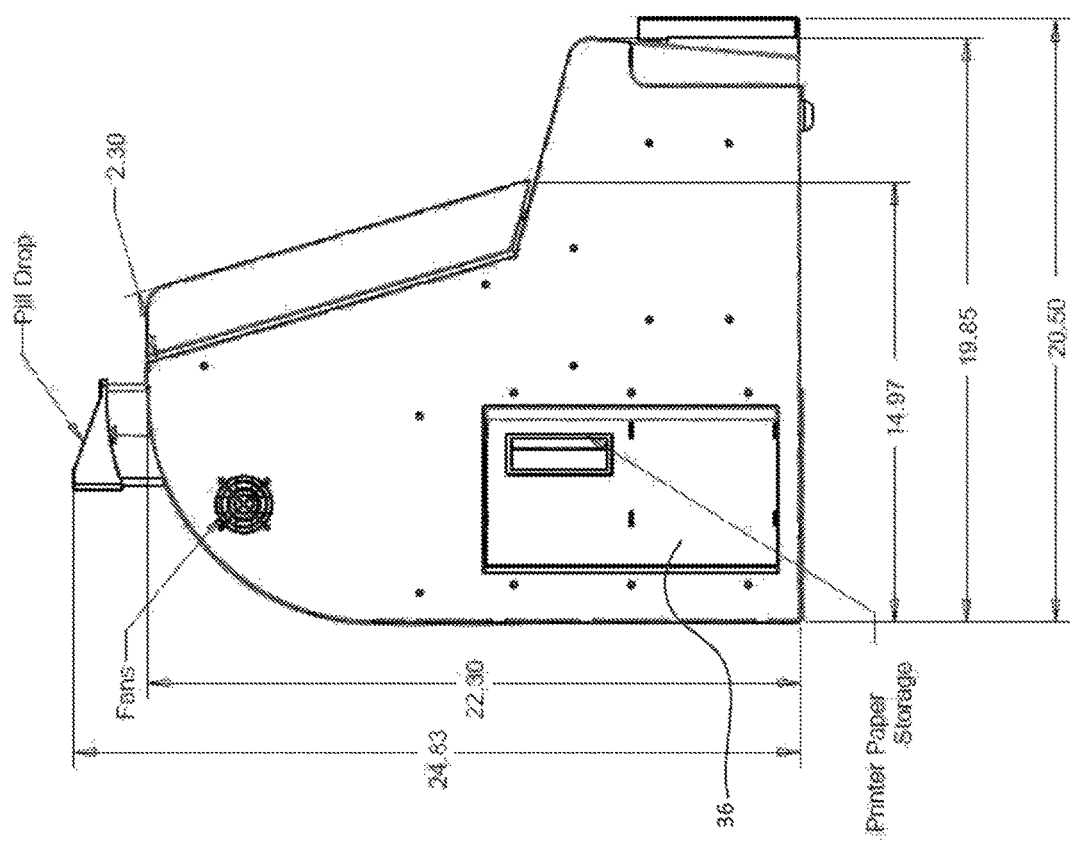
FIG. 3 illustrates a left side elevation view of the interactive kiosk of FIGS. 1 and 2, according to an illustrative embodiment.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Medication is often purchased by people with various illnesses, sicknesses, syndromes, or other maladies. As used herein, "medication" or "drugs" is not limited to prescribed drugs, but includes drugs purchased over-the-counter (e.g., without the need of a physician's approval). "Medication" and "drugs" also includes drugs in various forms, including pills, tablets, capsules, powders, creams, gels, liquids, or drugs administered via injection. People typically obtain their medications from a pharmacy, doctor's office, hospital, or other healthcare organizations which, in turn, obtains such medications directly or via a wholesaler from a pharmaceutical manufacturer. To facilitate pharmacies or other organizations having sufficient stock of medications on hand, pharmaceutical manufacturers frequently permit a pharmacy to return to the manufacturer thereof medication which remains unsold or unused after a period. Pharmaceutical manufacturers typically establish return policies which specify which medications may be returned and under what circumstances. For example, a return policy may state that a manufacturer will accept return of its unsold or expired medications provided that the medications are in their original packaging and unopened. The policy may further state that, if the returned medications meet the return criteria, the pharmaceutical manufacturer will refund to the pharmacy the purchase price of the returned medication or provide the pharmacy with a credit equivalent to the purchase price. The credit or refund value of returned medications may be substantial, both for an individual medication and in aggregated for a pharmacy or manufacturer. Because of this financial value, both the manufacturer and the pharmacy typically must accurately track, record, and audit detailed information about which medications are returned and at what time. A pharmacy is typically required to obtain written authorization from a pharmaceutical manufacturer before making the return of any particular medication. The pharmacy and the pharmaceutical manufacturer are also usually required by law or regulation to account for the whereabouts and safe destruction of returned medications to prevent theft or black market reselling. The medication return system is a time-consuming, labor-intensive process for both pharmacies and manufacturers, particularly when a typical pharmacy may return a few hundred to several thousand medications each year. Taken across a large pharmaceutical chain or manufacturer, the returned medications amount to millions of medications returned per year and several millions of dollars in credit value.

In some instances, a pharmaceutical manufacturer may choose to recall, or be required by a regulatory agency to recall, a medication after it has been provided to a pharmacy or other organization. For example, a pharmaceutical manufacturer may recall a medication because the medication is defective, incorrectly labelled, incorrectly packaged, or otherwise unfit for sale or use. In the case of a recall, the pharmaceutical manufacturer notifies each of its trading partners, requiring the trading partners to return the medications, usually for credit or refund of the purchase price. The pharmaceutical manufacturer and the pharmacy are typically required to keep records detailing which medications were returned, their condition, and at what time. Recall notifications are often mailed out by the pharmaceutical manufacturer to its trading partners. The traditional medication recall process is also time-consuming, labor-intensive, expensive, and slow.

Not all medication that is purchased is used by the customers. For example, some medication can be taken "as needed" and the customer may have purchased more than was needed. In another example, the medication may have been recalled by the manufacturer because of a defect. In yet another example, the medication may be past its expiration date. Regardless of the reason, some medications can also be returned by customers. For example, the customer can return medication to the pharmacy at which the medication was purchased.

In each case in which a medication is returned for credit by a pharmacy, recalled, or returned by a customer to a pharmacy, the pharmacy can process the medication by verifying that the medicine qualifies for a recall, refund, or return, counting or quantifying the medication, and sending the medication to the manufacturer thereof or for disposal or recycling. However, manually counting pills, verifying that the medicine is expired or recalled, preparing shipping, etc. can be time consuming for the pharmacy employees and for the customers. Furthermore, manually processing the medication permits human error. Various embodiments described herein automate the process of returning medication via a kiosk that, for example, can sit on a countertop of a pharmacy or in the warehouse or processing center of a pharmacy chain.

Traditionally, medications behind the counter at a pharmacy are periodically checked for expiration, short-dating, etc. For example, the pharmacist or pharmacy technician manually checks the labels on medications to see whether an item is expired or approaching its expiry date. In another example, the pharmacist or pharmacy technician scans barcodes on packaging of the drugs or inputs a lot number or other identifying information into a computer. The barcodes or lot number can be used to look up whether the drug should be removed from the shelf because the drug is expired or approaching its expiry date. For a drug recall, the pharmaceutical manufacturer may send a notice of recall to each pharmacy, usually by mail. Upon receipt, the pharmacist or pharmacy technician checks the inventory of the pharmacy for that medication. The pharmacist removes appropriate drugs (for return or recall) from the shelf, packages the drugs into a shipping container, and ships the container to a returns center for the pharmacy. For pharmacy chains, the returns center can service all stores that belong to the chain. The pharmacy store also prepares an inventory list of the items that are being returned. The inventory list can be sent to the returns center.

The returns center receives and opens the container with the drugs, then scans the barcodes on the drugs' packaging. The returns center then determines which drugs should be returned to which drug manufacturers. For each item, the returns center prepares returns authorizations to be sent to the drug manufacturers, which includes detailing for the manufacturer the number and type of items to be returned, the condition of each item (e.g., opened or unopened, full or partial, original packaging or prescription vial). The returns center may also verify the condition of each drug (for example, opened or unopened) and estimate the value of the drugs to be returned. The returns center then packages the drugs into a shipping container to send the drugs to either another returns center or the manufacturer.

After receipt of the drugs, the manufacturer (or its agent or contractor) verifies return authorizations that are sent with the drugs. Each return authorization is manually entered into a computer system of the manufacturer that records the information. Such information can be used to track actual drugs that are returned. The drugs are unboxed, barcodes are scanned, and the drugs are inventoried. The manufacturer may weigh the items to verify the weight indicated by the returns center. The manufacturer also visually inspects the drugs to ensure condition (e.g., that pills are whole) and to ensure that the drugs are what they are purported to be (e.g., and not candies). The manufacturer also verifies other information provided by the returns center, such as whether the packages are opened, whether all of the drugs of a package are present, whether the drugs are in their original packaging, etc. Each verification is recorded in a computer system along with whether the aspect being verified complies with the manufacturer's return policy. If the products comply with the manufacturer's return policy, then the manufacturer refunds or credits the pharmacy for the value of the item. But, if the manufacturer determines that the item does not comply with the return policy, then the pharmacy is not fully reimbursed, if at all. At the end of the process, the drugs are sent for secure disposal or destruction in compliance with relevant law.

Various embodiments described herein solve many of the problems and inefficiencies of the traditional system for returning drugs to the manufacturer. For example, some embodiments include a kiosk located at each pharmacy store that can perform functions typically performed in the pharmacy, at the pharmacy's returns center, and at the manufacturer or its agent or contractor. Thus, in some instances, the kiosk can eliminate the need to send the drugs to the returns center or the manufacturer, thereby increasing efficiency of the returns process for the pharmacy chain and manufacturer. In some instances, the kiosk can perform functions typically performed by the manufacturer (e.g., pill counting, recording quality and packaging, etc.). By performing functions performed by the manufacturer, the kiosk provides an additional level of verification or increases efficiency by reducing the amount of verification performed by the manufacturer. The kiosk can substantially shorten the time taken to process a return and issue credit therefor, reducing a process which typically takes ninety to one hundred and twenty days to as little as a week or less. In some embodiments described herein, the kiosk provides pharmacies and manufacturers with new information about when, where, and which types of drugs are most frequently returned, enabling them to improve their business practices. The kiosk can identify, in the pharmacy, which drugs qualify for credit once returned and which do not qualify for credit, thereby enabling the pharmacy to return the latter to stock for potential sale or sending such drugs directly for destruction, thus saving the costs of processing for return. Also, for recalls, pharmaceutical manufacturers can communicate electronically with the kiosk in the pharmacy to require recall of a medication. This saves time and reduces the risk of the pharmacy accidentally dispensing a recalled medication.

FIGS. 1-5 illustrate external views of a kiosk 10 that facilitates receiving, counting, labeling, and shipping returned medications. The kiosk 10 includes a housing 11, a pill drop opening 12, a touch screen 14, a finger scanner 15, a front-facing camera 18, a two-dimensional bar code scanner 17, a first label printer 20, a second label printer 22, a catch bin 24, a side drawer 26 with a handle 28, a front speaker 32, and a camera mount 34. In alternative embodiments, additional, fewer, and/or different elements may be used.

In an illustrative embodiment, the kiosk 10 is used to receive medication and information about the medication, and prepare the medication for return. The medication can be returned for any suitable reason, such as because a pharmacy has too much stock of a medication, because a medication is out of date, because of a customer return, because of a recall, etc. In some instances, the medication is returned to the manufacturer for a refund or credit.

In some embodiments, the kiosk 10 can include security features that limit use of the kiosk 10 to certain personnel, such as employees, doctors, pharmacists, customers, etc. For example, the finger scanner 15 can be used to verify the identity of a user. If the finger print scanned by the finger scanner 15 corresponds to a finger print stored on a database of the kiosk 10, the kiosk 10 (e.g., a processor within the kiosk 10) can determine that the user is an authorized user and allow access to the features of the kiosk 10.

In some embodiments, the front-facing camera 18 can be used to recognize the face of a user to determine that the user is an authorized user. For example, facial or retinal recognition can be used. In an alternative embodiment, the front-facing camera 18 can be used to record the user during use of the kiosk 10. The recording can be played back, for example, to determine who deposited a medication (or other object) into the kiosk 10, to verify proper use of the kiosk 10, to monitor for vandalism of the kiosk, etc. In some embodiments, the kiosk can include any suitable biometric scanner/input device, such as an eye scanner.

As previously mentioned, the kiosk 10 can be used to receive medication that is to be returned to a manufacturer of the medication. In an illustrative embodiment, a user logs into the system. For example, the user can use the touch screen 14 to indicate that the kiosk 10 is to be used. The user can supply log-in information such as a user ID, a password, a fingerprint via the finger scanner 15, etc. In some embodiments, a user does not log into the system, and the kiosk 10 can be used by any user. In some instances, the user can be an employee of a pharmacy store. In alternative embodiments, the user may be a customer of the pharmacy store (e.g., the person that the prescription is written for), an employee of the manufacturer, its agent, or contractor.

The user can input information about the medication to be returned. For example, the user can input information such as a name of the medication, a chemical of the medication, the lot number of the medication, the format of the medication (e.g., pill, caplet, capsule, tablet, liquid, powder, injectable, etc.), the size of the medication (e.g., the size or weight of each pill), an expiration date of the medication, an amount of the medication to be returned, a purchase date of the medication, etc. The user can input the information via, for example, the touch screen 14.

In some instances, the bar code scanner 17 can be used to scan a bar code of a medication. For example, the medication can be stored in a container with a label. The label can include a bar code. The bar code can be a unique to the medication supplied in the container when purchased. For example, the bar code scanner 17 can read the bar code, the kiosk 10 can convert the bar code into a medication identification (ID) number, and the kiosk 10 can use the ID number to look up information about the medication. In an illustrative embodiment, a database is used to associate the ID number with the information about the medication. In some embodiments, the database is stored in a memory device of the kiosk 10. In other embodiments, the database is stored remotely, and the kiosk 10 can access the database via, for example, network communications such as the Internet. In an illustrative embodiment, the information associated with the bar code includes the information necessary to process the medication, such as a manufacturer and lot number of the medication.

In an illustrative embodiment, the user inputs a lot number of the medication. The kiosk 10 can look up the lot number in a database and determine specifics of the medication. For example, once the kiosk 10 receives a lot number, the kiosk 10 can look up an image of the medication (e.g., of the packaging and/or the medication itself such as pills), an expected amount of the medication, and an expected weight. Such information can be presented to the user (e.g., via the touch screen 14), and the user can indicate whether the medication that the user has complies with such information. For example, the user can indicate whether the medication has been repackaged, whether the return is opened or unopened, whether the medication looks like the medication in the image provided by the kiosk 10, whether the medication packaging looks like the medication packaging in the image provided by the kiosk 10, etc.

In an illustrative embodiment, the kiosk 10 checks whether the medication associated with the information input by the user qualifies for a return, recall, exchange, or other type of processing. For example, the kiosk 10 can check with a manufacturer or a database, which can be remote or local, as to whether the lot number of the medication qualifies for return, recall, or exchange. For example, the user can scan a barcode on a bottle of pills. The manufacturer of the pills may have issued a recall of the medication that was sold. The bar code can include a type of medication (e.g., acetaminophen), a manufacturer of the medication, and a lot number of the medication. Based on such information, the kiosk 10 can determine that the medication was recalled or qualifies for a return and may be sent to the manufacturer for that reason.

In an example in which the medication is not approved for a return to the manufacturer, the user can be notified via a user interface (e.g., the touch screen 14 or the front speaker 32). In embodiments in which the kiosk 10 is located at a pharmacy store and is used by employees of the store, having the kiosk 10 verify that the medication qualifies for a return improves efficiency of the returns process. For example, traditionally, a store employee may send medication to the store's returns center regardless of whether the store's computer system indicates that the medication qualifies for a return. Similarly, in some instances, the returns center may send the medication to the manufacturer regardless of whether the medication qualifies for a return. Such processing by the returns center and the manufacturer and the shipment of the medication are wasted resources. In an embodiment in which the kiosk 10 is the primary or only method of returning medication to a manufacturer from a store, having the kiosk 10 refuse to process the medication prevents resources from being wasted down the processing chain, and increases efficiency. In instances in which the kiosk 10 determines that a medication does not qualify for a return, the kiosk 10 may provide the user the option to discard or destroy the medication (e.g., send the medication for disposal). In alternative embodiments, the kiosk 10 may provide the user with the option to return the medication to the manufacturer regardless of the determination of the kiosk 10 that the medication does not qualify for a return. In alternative embodiments, the kiosk 10 may provide the user with the option to return the medication to the pharmacy's stock or transfer the medication to another pharmacy for potential sale if the medication is still saleable. The kiosk 10 may also communicate with the manufacturer, pharmacy, or database and proactively alert the pharmacist when a medication is eligible for return instead of the pharmacist periodically checking inventory.

In an illustrative embodiment, once the kiosk 10 determines that the medication is to be received (e.g., qualifies for a return), the user can be instructed (e.g., via the touch screen 14) to put the medication into the pill drop opening 12. The user can pour or otherwise insert the pills into the pill drop opening 12 and the kiosk 10 receives the pills. As discussed in greater detail below, the kiosk 10 can count the pills and verify other information entered by the user such as the number of pills and the weight of the pills. Via images and information displayed on the touch screen 14, the kiosk can enable the user to verify the size, type, or color of the pills or that the pills are the medication that was recalled (e.g., via markings on the pills), etc. The user can insert a container (e.g., the container of the medication) into the catch bin 24. The kiosk 10 can count and verify the medication and dispense the pills into the container in the catch bin 24.

In an illustrative embodiment, the kiosk 10 can cause a label to be printed via the first label printer 20 or the second label printer 22. The label can include any suitable information. For example, the label can be a shipping label. The shipping label can be used to ship the container to the manufacturer of the medication, a disposal company for disposing of the medication, a collections depot for collecting medication for disposal, etc. In some embodiments, the label can include information such as the number of pills, the type of medication, a recall number of the medication, a lot number of the medication, etc. In an illustrative embodiment, the label includes a bar code that is associated with or contains such information.

In some embodiments, the kiosk 10 can be used for processing liquids, powders, injectable medicines, gels, creams, or capsules in blister packaging. For example, the side drawer 26 can include a scale for weighing medications. In an illustrative embodiment, a user enters information related to the medication as above. The user can indicate that the medication is a liquid (or powder). The side drawer 26 can be extended out from the housing 11, thereby exposing the scale. In alternative embodiments, any suitable scale can be used, such as a remote scale that communicates with the kiosk 10. The user can place a container with the liquid onto the scale. The scale can weigh the container with the liquid (or powder) and determine how much liquid (or powder) is in the container based on the weight and a known density of the medication. In some embodiments, the weight of the liquid or other medication is used to verify the amount of the liquid or other medication received from the user.

In an illustrative embodiment, the type of container is determined based on information received from the user. For example, the container can be determined to be the container that was provided to contain the medication when sold to the customer. The weight of the container can be looked up (e.g., via a database) and subtracted from the total weight measured by the scale to determine the weight of the medication. In another example, the medication can be placed into a container of a known weight (e.g., a container that is associated with the kiosk 10), and the known weight can be subtracted from the total weight measured to determine the weight of the medication. The medication can be a liquid, a powder, a pill, etc. The weight of the medication can be used to verify the amount and type of the medication by comparing the measured weight against the expected weight obtained from a database.

The camera mount 34 can be used to mount a camera that can capture an image of the medication on the scale. In alternative embodiments, a camera can be integrated into the housing 11 of the kiosk 10. In yet other embodiments, the camera may be mounted remotely or may be held by a user. The image captured by the camera can be used to verify the weight of the medication, the amount of the medication, the condition of the medication, and/or the condition of the packaging. In an illustrative embodiment, the camera can view into an opening of the container. In another embodiment, the container can be transparent or translucent. For example, the height and width of the medication within the container can be used to determine a volume of the medication. In some embodiments, the container is cylindrical. Based on the height of the medication in the container and the inside diameter of the container, the volume of the medication can be determined. The volume of the medication can be used to verify the weight of the medication using a volumetric weight of the medication which can be stored, for example, in a database.

In an illustrative embodiment, images taken by a camera (e.g., mounted on the camera mount 34) are used to verify the type of medication entered by a user. For example, a user may scan a barcode of a medication pill bottle, and the user can enter an amount of the medication to be returned. The user can use the scale (or any other suitable surface) to count the pills. While counting the pills, the camera can capture images of the pills. As described in greater detail below, the kiosk 10 can include a pill counter that can include a camera 58 that can be used to analyze the pills being counted. The images of the pills can be analyzed (e.g., by a processor of the kiosk 10) to determine or verify information such as a number of pills or a type of medication. For example, many pills, capsules, etc. have markings, impressions, printed information, etc. on the outside surface of the medication used to identify what the medication contains. In an illustrative embodiment, the camera captures an image of the pills and determines what the markings on the pills are. The kiosk 10 can use the markings on the pills along with other suitable information such as the shape and color of the pills to determine what medication the pills have. For example, the kiosk 10 can use a camera to determine that the pills are round, off-white color, and are imprinted with a "U" on one side and "171" on the other (e.g., from the perspective of the camera, some pills contain a "U" and others contain "171"). Based on such information, the kiosk 10 can determine (e.g., via a look-up table or database) that the pills contain Memantine. In some instances, the pills can be imprinted with information that can be used by the kiosk 10 to determine any other suitable information, such as a strength of the pills. Such information can be used to verify the information input by the user or information included in the scanned barcode.

In some instances, the camera can be used to verify the quality and/or type of packaging. For example, if a user indicates that medication in a bubble seal package is unopened, the camera can be used to capture images of the foil seal on the package. The images can be used to verify that the medication is unopened.

In some instances, the camera is used to capture images of the medication, but the kiosk 10 does not perform image processing to determine that the medication in the images satisfies the return criteria. For example, in an illustrative embodiment, the kiosk 10 can receive (e.g., from a database) an image of the medication that is being processed. The kiosk 10 may receive the image based on the lot number or other identifying information received. The kiosk 10 may display the image to the user so that the user can verify that the medication or packaging being processed looks like the medication or packaging in the image. In such an embodiment, the user may input into the kiosk an indication of whether the medication being processed is similar or the same to that in the image.

Figure 4:
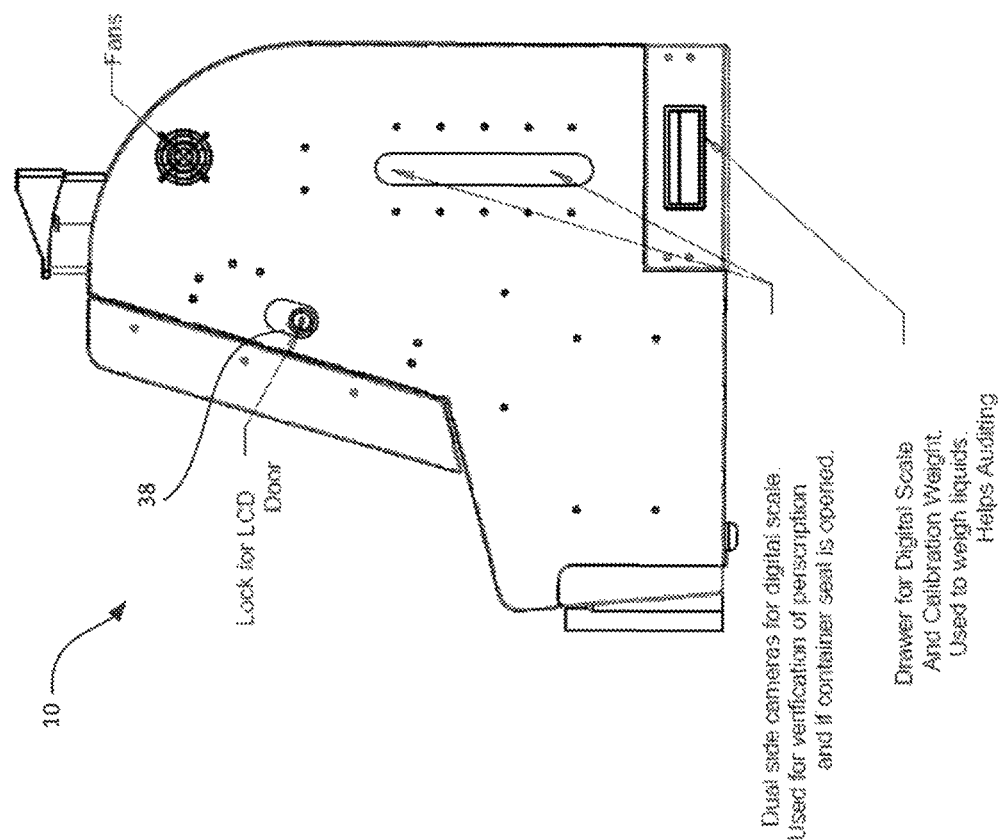
FIG. 4 illustrates a right side elevation view of the interactive kiosk of FIGS. 1-3, according to an illustrative embodiment.
Figure 5:
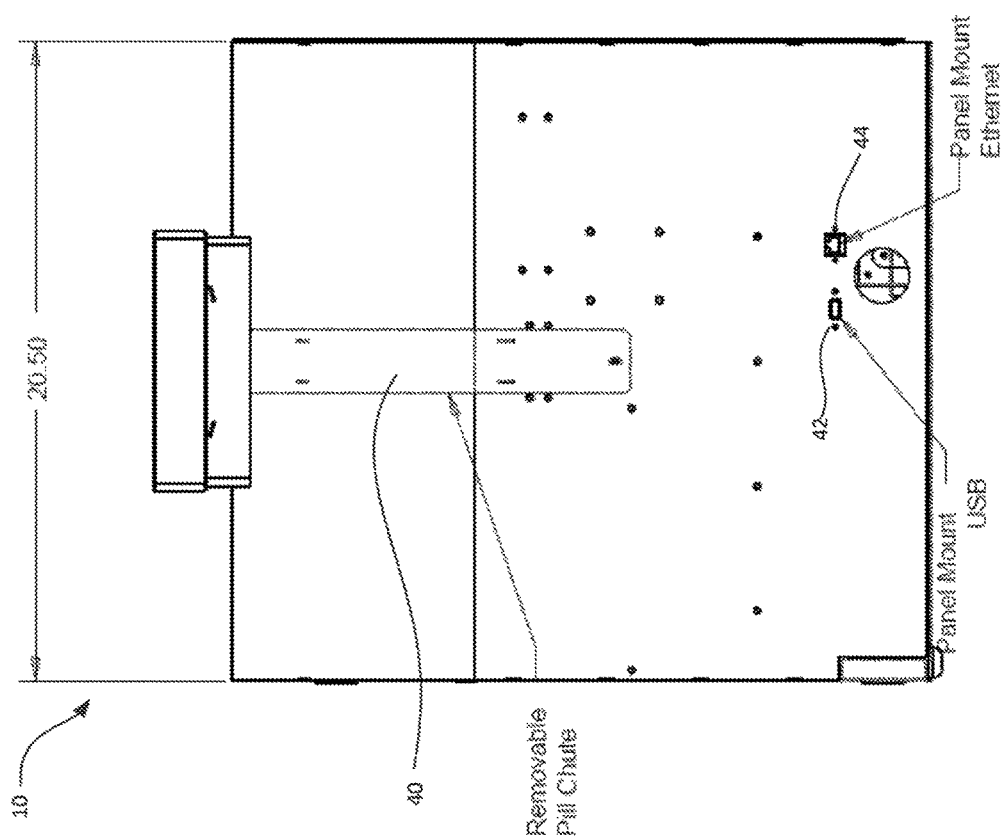
FIG. 5 illustrates a rear elevation view of the interactive kiosk of FIGS. 1-4, according to an illustrative embodiment.

In some embodiments, the kiosk 10 may further include a vent 30 configured to permit active or passive cooling or ventilation of the housing 11. Kiosk may further include a front speaker 32 for conveying audio information to the user. As shown in FIG. 4, the touch screen 14, which may be an LCD device, may be accessed via a hinged door, and which may be locked at lock 38, according to an illustrative embodiment. As illustrated in FIG. 5, the rear of the housing 11 may include a pill chute 40 which can be removable for maintenance, cleaning, and/or unjamming. The kiosk 10 may further include communications ports such as a USB port 42 and/or an Ethernet port 44, according to an illustrative embodiment.

Figure 6:
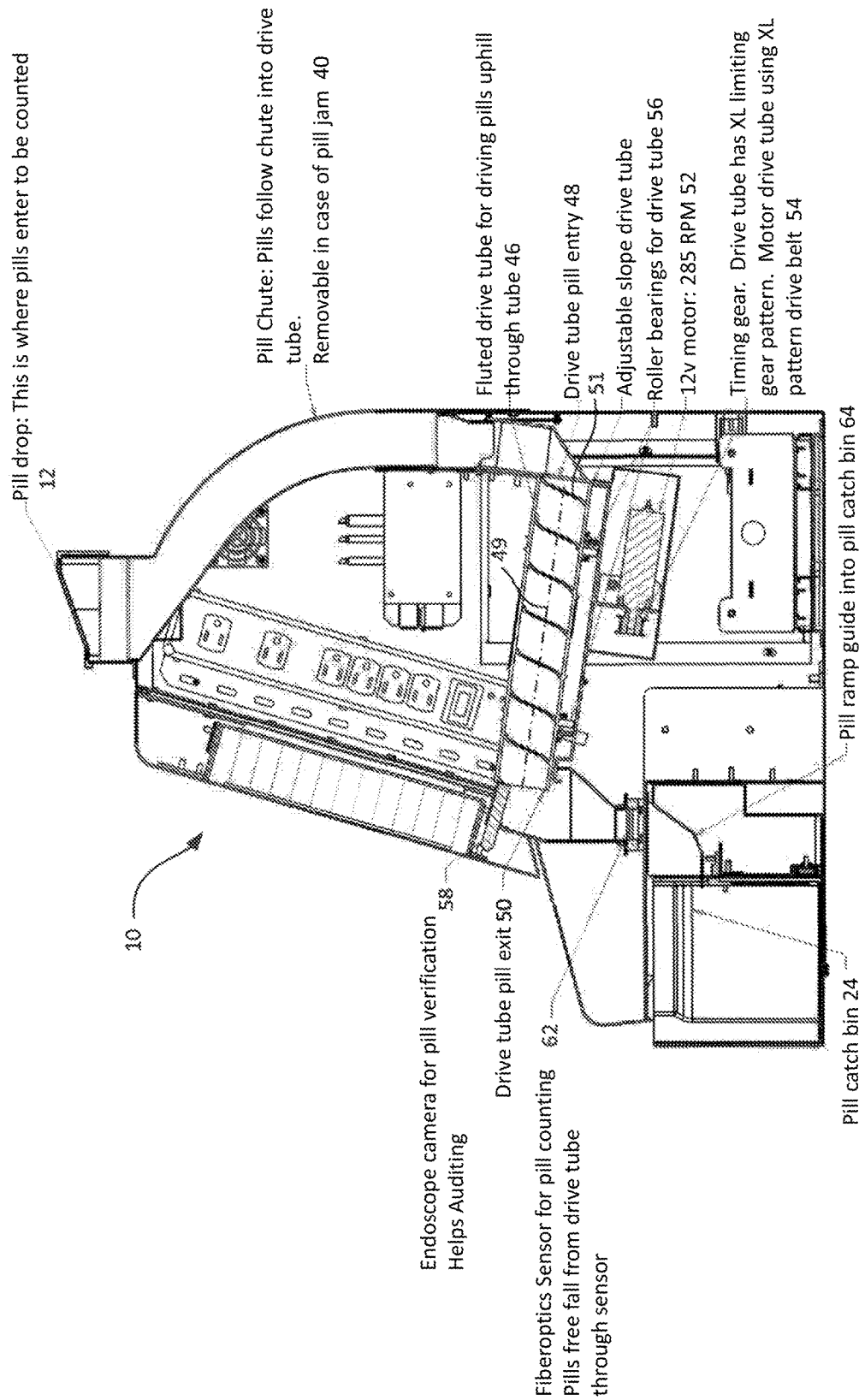
FIG. 6 illustrates a right side elevation cross-sectional view of the interactive kiosk of FIGS. 1-5, according to an illustrative embodiment.
Figure 7:
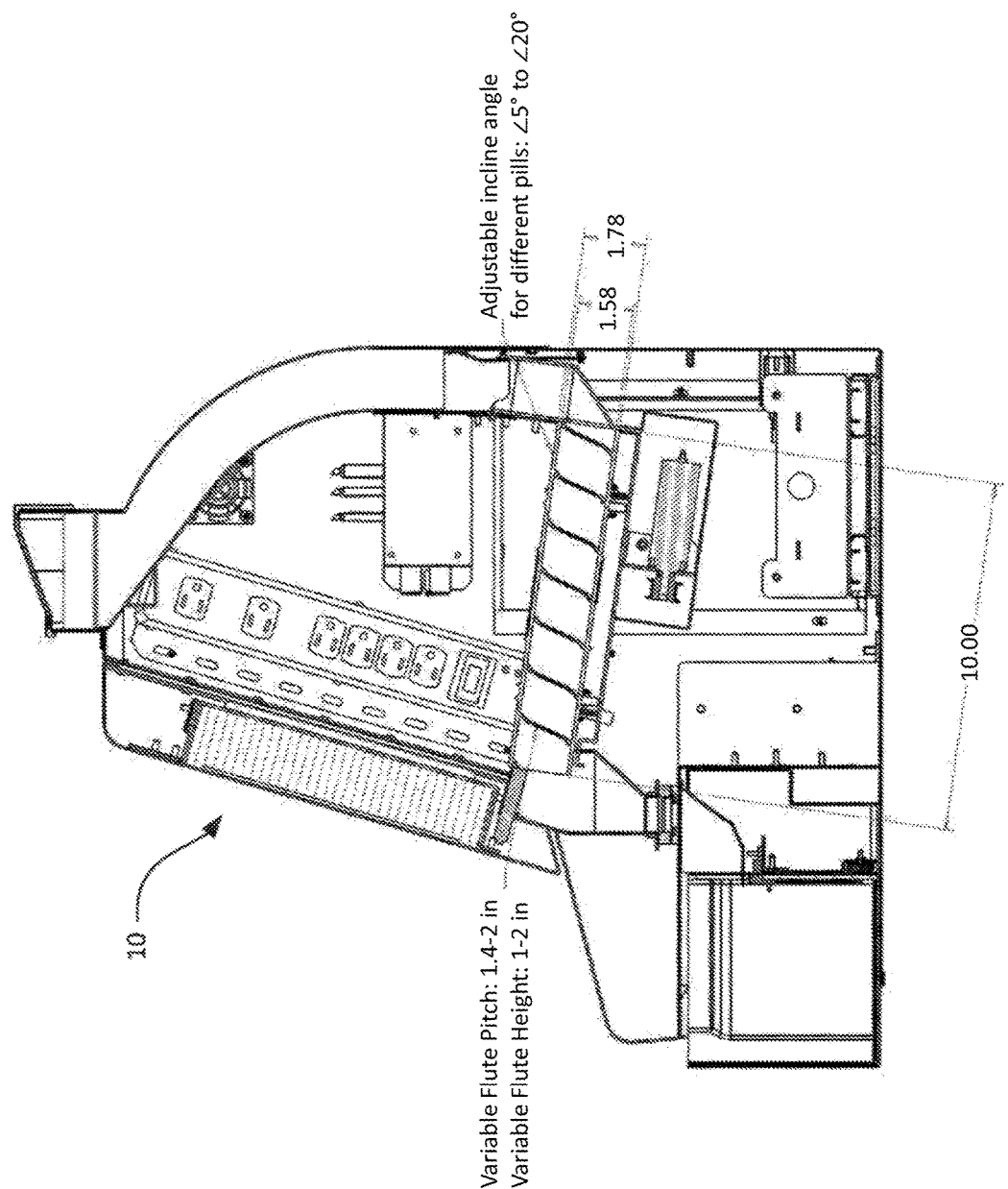
FIG. 7 illustrates the right side elevation cross-sectional view of the interactive kiosk of FIGS. 1-6 showing additional detail, according to an illustrative embodiment.

FIG. 6 illustrates a right side elevation cross-sectional view of the interactive kiosk of FIGS. 1-5, according to an illustrative embodiment. FIG. 7 illustrates the right side elevation cross-sectional view of the interactive kiosk of FIGS. 1-6 showing additional detail, according to an illustrative embodiment. The kiosk 10 includes a pill drop opening 12, a pill chute 40, a drive tube 46, an entry opening 48, an exit opening 50, a motor 52, a timing gear system 54, roller bearings 56, an endoscope camera 58, a fiber optic sensor 62, and a pill ramp guide 64. In alternative embodiments, additional, fewer, and/or different elements may be used.

As mentioned above, the user can enter information related to medication that is to be processed by the kiosk 10. FIGS. 6 and 7 show a pill counting system for counting and quantifying the medication. The counting system can be used to count pills, capsules, caplets, tablets, etc. A user can drop the pills into the pill drop opening 12. Gravity causes the pills to fall through the pill chute 40 and into an entry opening 48. In an illustrative embodiment, if enough pills are dropped into the pill drop opening 12, the pills can stack up behind the entry opening 48 and into the pill chute 40.

Pills can enter the drive tube 46 via the entry opening 48. The drive tube 46 rotates. The motor 52 is mechanically attached to the drive tube 46 to rotate the drive tube 46. In an illustrative embodiment, the motor 52 is a twelve Volt motor that rotates at a speed of 285 rotations per minute (RPM). In alternative embodiments, any suitable motor voltage can be used (e.g., alternating current voltage) and any suitable rotational speed can be used.

For example, the kiosk 10 can include a timing gear system 54 to mechanically connect the motor 52 with the drive tube 46. In alternative embodiments, any suitable mechanical connection can be used, such as gears, belts, clutches, etc. The inside surface of the drive tube 46 includes a ridge 51 that runs along the length of the drive tube 46 in a helical direction. For example, the ridge 51 can operate as an auger or screw to move pills along the drive tube 46 when the drive tube 46 rotates. In an illustrative embodiment, the ridge 51 is a helical flute shape. In the embodiment shown in FIGS. 6 and 7, the drive tube 46 is mounted on the roller bearings 56 that reduce friction of the rotating drive tube 46 and facilitate the rotation of the drive tube 46.

As shown in FIGS. 6 and 7, the drive tube 46 is angled upward. For example, the centerline 49 of the drive tube 46 is not parallel to the bottom surface of the kiosk 10. As the drive tube 46 rotates, pills travel along and up the drive tube 46 from the entry opening 48 to the exit opening 50. The exit opening 50 is higher than the entry opening 48. Any suitable incline angle can be used for the drive tube 46. In some embodiments, the drive tube 46 is not inclined.

As the pills are transferred from the entry tube 48, the pills spread out (e.g., are not transferred in bulk). In an illustrative embodiment, the pills traveling on the drive tube 46 are not stacked on one another. The angle of the drive tube 46 can be configured to facilitate the spreading out of the pills. In an illustrative embodiment, the angle of the drive tube 46 is adjustable. For example, varying pill sizes and shapes may spread out along the drive tube 46 at differing rates. In some embodiments, the angle of the drive tube 46 can be adjusted manually.

In some embodiments, the angle of the drive tube 46 can be adjusted automatically. For example, the camera 58 can be used to monitor the pills within the drive tube 46. The camera 58 can be used to capture images that can be used to determine whether the pills are bunching or stacking on top of one another within the drive tube 46. In an illustrative embodiment, if it is determined that the pills are stacking within the drive tube 46, the angle of the drive tube 46 can be increased to spread out the pills along the drive tube 46. In some embodiments, if the pills are spread too thin (e.g., the rate of pills driven up the drive tube 46 is below a threshold rate), the angle of the drive tube 46 can be decreased. Any suitable range of angles for the drive tube 46 can be used. For example, the angle of the drive tube 46 can be adjusted from 8° to 20° from horizontal. In other examples, the angle of the drive tube 46 can be 0°, 5°, 25°, 30°, etc. Any suitable device can be used to adjust the angle of the drive tube 46, such as a solenoid or stepper motor.

Once the pills are transferred to the top of the drive tube 46, the pills exit the drive tube 46 via the exit opening 50. The pills can drop through the fiber optic sensor 62, which can count the pills that fall through the fiber optic sensor 62. For example, the pills can fall through the fiber optic sensor 62 at a rate at which the fiber optic sensor 62 can count the pills that fall through. For example, the angle of the drive tube 46 can be adjusted automatically to increase the rate at which pills fall through the fiber optic sensor 62 without exceeding an upper threshold rate at which the fiber optic sensor 62 cannot count the pills that fall through (e.g., a rate at which more pills fall through the fiber optic sensor 62 than are counted by the fiber optic sensor 62). The fiber optic sensor 62 can count the pills that were entered into the pill drop 12. The counted pills can be used to verify an amount of the medication. For example, the number of pills counted can verify the amount of medication provided to the kiosk 10 via the touch screen 14 and/or the bar code scanner 17.

After the pills fall through the fiber optic scanner 62, the pills fall across the pill ramp guide 64 and into the pill catch bin 24. In an illustrative embodiment, the pill catch bin 24 is the pill container that was originally provided to the customer to hold the medication. In alternative embodiments, the pill catch bin 24 is a removable bin of the kiosk 10. The pill catch bin 24 with the pills can be removed, and the pills can be removed from the pill catch bin 24 (e.g., by pouring out the pills into a container or bag).

In an illustrative embodiment, the endoscope camera 58 is positioned to capture images of the inside of the drive tube 46. The images can be used for any suitable purpose. For example, the images can be stored in a memory and recalled later (e.g., to be displayed) for use by maintenance personnel to monitor the functioning of the drive tube 46. In an illustrative embodiment, the processor receives images from the endoscope camera 58 and analyzes the images to determine the distribution of pills along the drive tube 46. For example, the processor can determine whether the pills are bunching up along the drive tube 46 or are too dispersed (e.g., thereby reducing efficiency). The processor can cause the angle of the drive tube 46 to change based on the determined distribution of the pills. For example, a step motor or other device can be used to adjust the angle of the drive tube 46.

In an illustrative embodiment, images captured by the endoscope camera 58 are stored along with other information related to the pills that were in the drive tube 46 when the images were captured. For example, the images can be stored along with the information associated with the bar code on the package of the pills, the information entered by the user, whether the pills qualify for return, etc. In such an embodiment, the images can be transmitted to a manufacturer or a returns center as evidence or verification that the pills are what the pharmacy store says they are. If the manufacturer determines that the pills do not qualify for a return for some reason, the images can be used to determine why. For example, if the manufacturer receives information related to a return and receives a package with the medication that is to be returned and if the manufacturer determines that the medication is actually pill-shaped mint candy, the manufacturer can use the images taken by the endoscope camera 58 to determine that, at least at the kiosk 10, the items being counted were (or were not) medication. In such a scenario, the manufacturer or pharmacy store may use such information to detect theft or fraud by individuals.

FIG. 7 illustrates that the drive tube 46 may include an inner diameter of 1.58 inches, and an outer diameter of 1.78 inches, according to an illustrative embodiment. The length of the drive tube 46 may be ten inches, according to an illustrative embodiment. The pitch of the flute 51 may vary, and may be, for example, from 1.4 to 2.0 per inch. The height of the flute 51 may vary, and may be, for example, from 0.1 to 0.2 inches tall above the inner diameter of the drive tube 46. According to some embodiments, the incline of the central axis 49 of the drive tube with respect to the horizontal (i.e. the ground surface horizontal level) is adjustable, for example from eight degrees to twenty degrees. In an illustrative embodiment, the drive tube 46 may be adjusted automatically by the kiosk 10 based on known information about pill size and shape from on the user-entered information, or from images captured by the endoscope camera 58.

Figure 8:
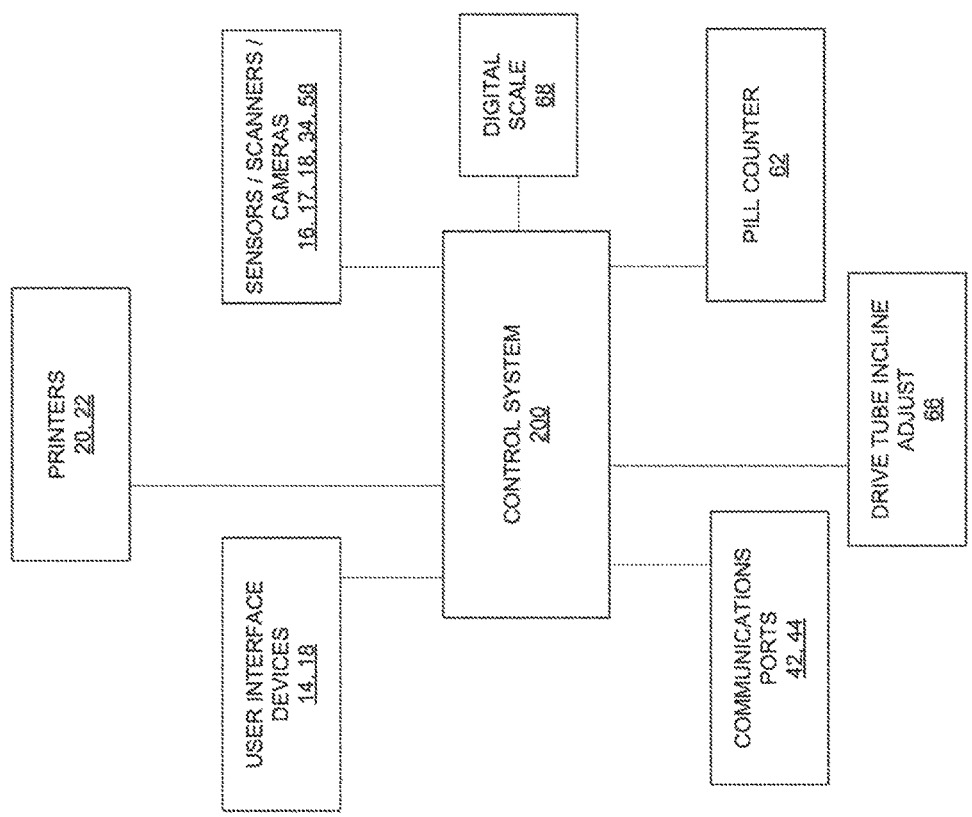
FIG. 8 illustrates a kiosk system, according to an illustrative embodiment.

FIG. 8 illustrates a kiosk control system, according to an illustrative embodiment. A control system 200 is communicably coupled to user interface devices 14, 18, printers 20, 22, sensors, scanners, and cameras 16, 17, 18, 34, and 58, pill counter 62, communications ports 42, 44, drive tube incline adjustment mechanism 66, and/or digital scale 68, according to an illustrative embodiment. Control system 200 may be a personal computer or other computing device, according to an illustrative embodiment.

The control system 200 is capable of executing instructions to perform the steps and methods described herein, in whatever order, and excluding one or more steps and/or including one or more additional steps or repetitions of steps, according to an illustrative embodiment. The control system 200 receives information or signals and, based on such information or signals, sends out control signals to cause the hardware to operate accordingly, as described herein. The control system may also receive information from other hardware, not shown. The control system 200 may also rely on other sensors or signals not expressly shown, but which are apparent to one of ordinary skill in the art based on the present disclosure. For example, positional sensors may be used to provide the control system 200 with the two-dimensional (or three-dimensional) position of any piece of hardware described herein.

Figure 9:
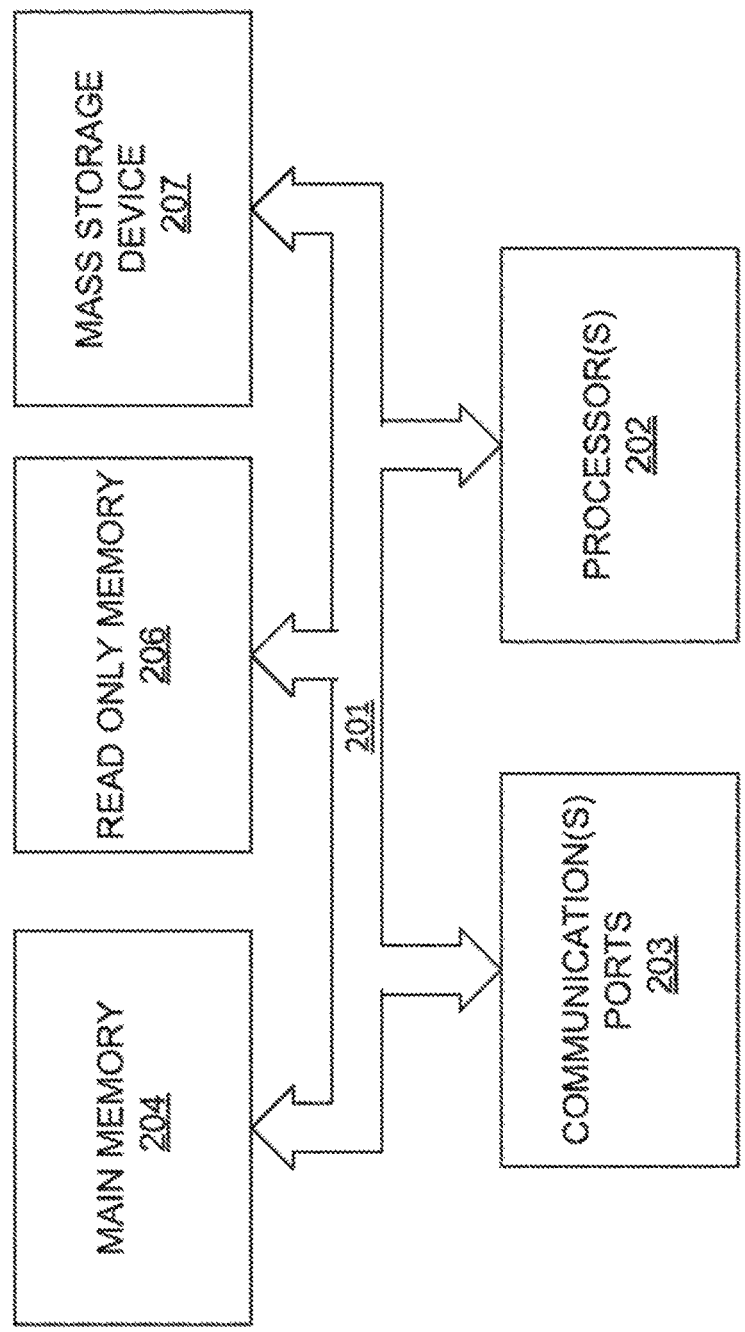
FIG. 9 illustrates a computer system, according to an illustrative embodiment.

FIG. 9 is an example of a computer system 200 with which embodiments of the present disclosure may be utilized. Computer system 200 represents an exemplary computer, which may operate as controller 200 in order to receive inputs (e.g. from sensors) and/or provide outputs (e.g. to control the printers, rotation of the drive tube 46, and/or incline of the drive tube 66). In this simplified example, the computer system 200 comprises a bus 201 or other communication means for communicating data and control information, and one or more processing devices 202, such as a well-known processor, Application Specific Integrated Circuit (ASIC), a field programmable gate array (FPGA), or the like, coupled with bus 201.

In this simplified embodiment, computer system 200 further comprises a random access memory (RAM) or other dynamic storage device (referred to as main memory 204), coupled to bus 201 for storing information and instructions to be executed by processing device 202. Main memory 204 also may be used for storing temporary variables or other intermediate information during execution of instructions by processor(s) 202.

Computer system 200 can also include a read only memory (ROM) 206 and/or other static storage device coupled to bus 201 for storing static information and instructions for processing device 202. A mass storage device 207, such as a magnetic disk or optical disc and its corresponding drive, may also be coupled to bus 201 for storing instructions and information, such as configuration files, a key store and registration database, and the like.

One or more communication ports 203 may also be coupled to bus 201 for supporting network connections and communication of information to/from the computer system 200 by way of a communication network, such as a Local Area Network (LAN), Wide Area Network (WAN), or the Internet, for example. The communication ports 203 may include various combinations of well-known interfaces, such as one or more modems to provide network access, one or more 10/100 Ethernet ports, one or more Gigabit Ethernet ports (fiber and/or copper), or other well-known network interfaces commonly used in internetwork environments. In any event, in this manner, the computer system 200 may be coupled to a number of other network devices, communication devices, clients, NTMs, and/or servers via a conventional communication network infrastructure. Optionally, operator and administrative interfaces (not shown), such as a display, keyboard, and a cursor control device, may also be coupled to bus 201 to support direct operator interaction with computer system 200. Other operator and administrative interfaces can be provided through network connections connected through communication ports 203. Finally, removable storage media (not shown), such as one or more external or removable hard drives, tapes, floppy disks, magneto-optical discs, compact disk-read-only memories (CD-ROMs), compact disk writable memories (CD-R, CD-RW), digital versatile discs or digital video discs (DVDs) (e.g., DVD-ROMs and DVD+RW), Zip disks, or USB memory devices, e.g., thumb drives or flash cards, may be coupled to bus 201 via corresponding drives, ports or slots.

Figure 10:
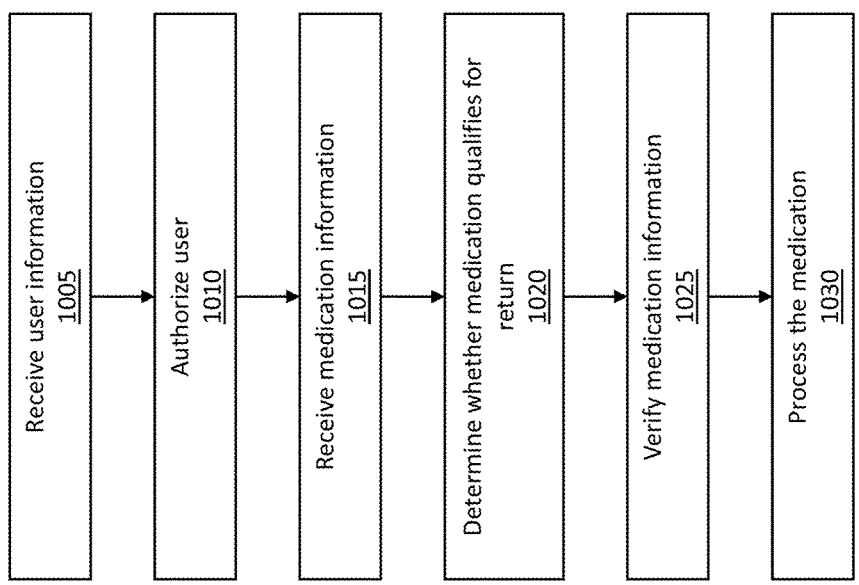
FIG. 10 is a flow diagram of a method of processing medication in accordance with an illustrative embodiment.

FIG. 10 is a flow diagram of a method of processing medication in accordance with an illustrative embodiment. In alternative embodiments, additional, fewer, and/or different operations may be performed. Also, the use of a flow chart and arrows is not meant to be limiting with respect to the flow or order of operations or information. For example, in some embodiments, two or more operations may be performed simultaneously.

In an operation 1005, user information is received. For example, a user can enter into a kiosk a username and log-in credentials such as a password, a fingerprint scan, a facial scan, an eye scan, etc. In an operation 1010, the user is authorized. For example, the log-in credentials can be used to authorize the user to use the kiosk. Authorized users can be, for example, employees, owners of the kiosk, patients, etc.

In an operation 1015, medication information is received. In an illustrative embodiment, the user can input medication information via a user input such as a keyboard, mouse, touch screen, etc. In an alternative embodiment, the user can input the medication information via a bar code scanner. For example, a bar code on a label of the medication packaging can be scanned. The medication information can include any suitable information such as a type of medication (e.g., anti-inflammatory, steroid, pain relief, etc.), a chemical formula (e.g., acetaminophen, heparin, etc.), a brand name, a manufacturer, a manufacture lot number, a pill size, an amount prescribed, an amount remaining, condition of the packaging (e.g., unopened in original packaging from the manufacturer, opened in original packaging, repackaged), etc.

In an operation 1020, the kiosk determines whether the medication associated with the medication information qualifies for a return. For example, based on the lot number, product type, manufacturer, expiration date, weight, pill count, and packaging type, the kiosk can query a database to determine whether the medication qualifies for a return. In some embodiments, the kiosk can determine how much money, if any, should be refunded for the return. In some instances, the kiosk determines that the medication does not qualify for a return, but can be sent to a disposal facility. In other instances, the kiosk determines that the medication does not qualify for a return, but may be returned to stock or transferred to a different pharmacy for potential sale.

In an operation 1025, the medication information is verified. In an illustrative embodiment, various components of the kiosk and/or components in communication with the kiosk can be used to count pills, weigh the medication, determine an amount of the medication, verify that markings on the pills corresponds with the received medication information, capture images of the packaging to verify the condition of the packaging, or otherwise gather information to verify some or all of the medication information. In some embodiments, one or more cameras can be used to video a user of the kiosk to verify that the medication that was measured is the same medication that is packaged into a shipping container.

In an operation 1030, the medication is processed. For example, whether the medication qualifies for a return can be verified. That is, the kiosk may have determined that the medication qualifies for a return based on the medication information received in the operation 1015, but some of the information may not have been verified in the operation 1025. For example, the medication information may have indicated that the medication included 100 pills, but, the kiosk may have determined that the medication included only 16 pills (e.g., via a pill counter). Following the example, in the operation 1030, the kiosk can determine whether a partial bottle of the medication qualifies for a return. In an illustrative embodiment, the operation 1030 includes printing a label such as a shipping label.

In an illustrative embodiment, the operation 1030 includes transmitting the medication information and the information used to verify the medication information. For example, the kiosk can transmit, to a remote server (e.g., a server of the medication manufacturer, the pharmacy chain, or the processor of the return) the medication information, the determined weight of the medication, images of the medication and/or packaging, a pill count determined by the kiosk, a video of the user of the kiosk, etc. In some embodiments, the medication information and the verification information can be accessed by the manufacturer (or manufacturer's agent) to pre-approve a return. For example, based on the verification information, the manufacturer can determine that the medication qualifies for a return and can transmit to the kiosk an indication of the pre-approval. Based on the pre-approval, the kiosk can facilitate shipment of the medication (e.g., by printing a return receipt, by printing a shipping label, etc.). In an illustrative embodiment, the stored information can be used during an audit of the return to, for example, ensure proper handling of the return or investigate fraud.

In an illustrative embodiment, any of the operations described herein can be implemented at least in part as computer-readable instructions stored on a computer-readable memory. Upon execution of the computer-readable instructions by a processor, the computer-readable instructions can cause a node to perform the operations.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to disclosures containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the disclosure be defined by the claims appended hereto and their equivalents.

What is claimed is:

1. A kiosk comprising:
   a user interface device that receives information from a user;
   a display that displays information to the user;
   a first camera;
   a second camera;
   a scale;
   a transceiver that communicates with a database; and
   a processor operatively coupled to the user interface device, the display, the first camera, the scale, and the transceiver, wherein the processor includes programmed instructions to:
      receive, from the user interface device, medication information, wherein the medication information comprises an indication of whether packaging of a medication has been opened;
      determine an identity of the medication associated with the medication information by determining, via the database, that the medication associated with the medication information satisfies criteria, wherein the criteria are provided to the database by a manufacturer of the medication, and wherein the criteria comprises an expected weight criterion of the medication and a visual criterion of the medication;
      receive, from the first camera, an image of the medication;
      receive, from the second camera, an image of the packaging of the medication;
      receive an indication that the medication satisfies the visual criterion;
      receive, from the scale, a weight of the medication;
      determine that the weight of the medication satisfies the expected weight criterion;
      cause the display to display an indication that the medication satisfies the criteria based at least in part on the determination that the image of the medication satisfies the visual criterion and the determination that the weight of the medication satisfies the expected weight criterion; and
      cause the transceiver to transmit the medication information, the image of the medication, the image of the packaging of the medication, and the weight of the medication to the database.

2. The kiosk of claim 1, further comprising a pill counter, wherein the criteria further comprise an expected number of pills criterion, and wherein the processor further includes programmed instructions to:
   receive, from the pill counter, a number of pills of the medication; and
   determine that the number of pills satisfies the expected number of pills criterion.

3. The kiosk of claim 2, wherein the pill counter comprises a drive tube with a helical flute that distributes and conveys pills to an optical pill counter.

4. The kiosk of claim 3, wherein the first camera comprises an endoscope camera that captures images of pills in the drive tube.

5. The kiosk of claim 3, wherein an angle of the drive tube is adjustable, and wherein the processor includes programmed instructions to adjust the angle of the drive tube based on images of the pills in the drive tube.

6. The kiosk of claim 1, wherein the weight of the medication includes a weight of a container.

7. The kiosk of claim 1, wherein the criteria further comprises a status of the packaging of the medication criterion, and wherein the processor includes programmed instructions to determine, based at least in part on the image of the packaging of the medication, that the packaging of the medication satisfies the status of the packaging of the medication criterion.

8. The kiosk of claim 1, wherein the medication comprises pills, and wherein the visual criterion comprises a symbol on the pills.

9. The kiosk of claim 8, wherein the symbol is at least one of imprinted into the pills, a raised symbol on the pills, or printed onto the pills.

10. The kiosk of claim 1, further comprising a printer, wherein the processor further includes programmed instructions to cause the printer to print a shipping label based at least in part on the determination that the image of the medication satisfies the visual criterion and the determination that the weight of the medication satisfies the expected weight criterion.

11. The kiosk of claim 1, wherein the database is stored on a plurality of servers.

12. The kiosk of claim 1, wherein the processor further includes programmed instructions to determine that the medication qualifies for at least one of a refund, a recall, or a return based at least on the medication information.

13. The kiosk of claim 1, wherein to receive the indication that the medication satisfies the visual criterion, the processor further includes programmed instructions to determine that the image of the medication satisfies the visual criterion.

14. The kiosk of claim 1, wherein the indication that the medication satisfies the visual criterion is received from the user interface device.

15. A method comprising:
 receiving, from a user interface device that receives information from a user, medication information, wherein the medication information comprises an indication of whether packaging of a medication has been opened;
 determining an identity of the medication associated with the medication information by determining, via a remote database, that the medication associated with the medication information satisfies criteria, wherein the criteria are provided to the remote database by a manufacturer of the medication, and wherein the criteria comprises an expected weight criterion of the medication and a visual criterion of the medication;
 receiving, from a first camera, an image of the medication;
 receiving, from the second camera, an image of the packaging of the medication;
 receiving an indication that the image of the medication satisfies the visual criterion;
 receiving, from a scale, a weight of the medication;
 determining that the weight of the medication satisfies the expected weight criterion;
 causing a display to display an indication that the medication satisfies the criteria based at least in part on the determination that the image of the medication satisfies the visual criterion and the determination that the weight of the medication satisfies the expected weight criterion; and
 transmitting, to the remote database, the medication information, the image of the medication, the image of the packaging of the medication, and the weight of the medication.

16. The method of claim 15, wherein the criteria further comprises an expected number of pills criterion, and wherein the method further comprises:
 receiving, from a pill counter, a number of pills of the medication; and
 determining that the number of pills satisfies the expected number of pills criterion.

17. The method of claim 15, wherein the weight of the medication includes a weight of a container.

18. The method of claim 15, wherein the criteria further comprises a status of the packaging of the medication criterion, and wherein the method further comprises determining, based at least in part on the image of the packaging of the medication, that the packaging of the medication satisfies the status of the packaging of the medication criterion.

* * * * *